United States Patent [19]

Kohmura et al.

[11] 4,154,717

[45] May 15, 1979

[54] HYDRAULIC DENTAL CEMENT COMPOSITION

[75] Inventors: Tamotsu Kohmura, Yao; Hiroshi Nakanaga, Takarazuka; Kazuhiro Ida, Toyonaka, all of Japan

[73] Assignee: Sankin Industry Company, Limited, Osaka, Japan

[21] Appl. No.: 841,895

[22] Filed: Oct. 13, 1977

[30] Foreign Application Priority Data

Nov. 16, 1976 [JP] Japan ............................ 51-138002

[51] Int. Cl.² .......................... C08K 3/22; C08K 3/36
[52] U.S. Cl. ........................ 260/42.13; 260/29.6 H; 260/29.6 M; 260/42.43; 260/42.52
[58] Field of Search ............. 260/29.6 M, 29.6 H, 260/42.43, 998.11, 42.52, 42.13

[56] References Cited

U.S. PATENT DOCUMENTS

| | | | |
|---|---|---|---|
| 3,741,926 | 6/1973 | Jurecic | 260/29.6 M |
| 3,751,391 | 8/1973 | Smith | 260/998.11 |
| 3,962,267 | 6/1976 | Suzuki et al. | 260/998.11 |
| 4,016,124 | 5/1977 | Crisp et al. | 260/29.6 H |
| 4,017,454 | 4/1977 | Muller | 260/998.11 |

FOREIGN PATENT DOCUMENTS 1316129  5/1973  United Kingdom.

*Primary Examiner*—James H. Derrington
*Attorney, Agent, or Firm*—Oblon, Fisher, Spivak, McClelland & Maier

[57] ABSTRACT

A hydraulic dental cement composition which comprises a mixture of a dental cement powder having silicon oxide for its essential constituent and a setting agent powder having polyacrylic acid for its essential constituent is disclosed. This composition is of high compression strength due to the silicon dioxide contained therein, and its own pulverulence makes it excellent in workability because it has only to be kneaded with water to be placed into a useable form. Addition of zinc oxide or the like enhances the resistance to deterioration of the composition.

12 Claims, 1 Drawing Figure

HYDRAULIC DENTAL CEMENT COMPOSITION

BACKGROUND OF THE INVENTION

1. Field of the Invention

This invention relates to a hydraulic cement composition for dental use, and in particular to a cement composition having good compression strength and workability. The composition is suitable for producing dental fillings, inlays, or crowns. The quantity of water required for kneading will vary depending on the use of the respective proposes.

2. Description of the Prior Art

In the past, zinc phosphate-based cements predominated in dental use. However, it can be seen from West German Patent Laid Open No. 1617688 that rapid development of polycarboxylate cements has taken place in recent times. The advantage of polycarboxylate cement is that it is less of a stimulant to dental pulpa and adheres better to dentine compared to zinc phosphate cement. Nevertheless, it has the disadvantage that its compression strength is lower by about 400-500 kg/cm$^2$ than that of zinc phosphate cement which has a compression strength of about 1200-1300 kg/cm$^2$. In addition, polycarboxylate cement used heretofore was usually employed as a 50% aqueous solution in polyarylic acid (viscosity: 5000 cps), with the result that the viscosity of its kneading solution was considerably higher than that of zinc phosphate cement. This caused difficulty in kneading and also caused reduction in both compression strength and adhesion because of the inclusion of air bubbles in the course of kneading or molding.

A need, therefore, continues to exist for a polycarboxylate cement composition having high compression strength.

SUMMARY OF THE INVENTION

Accordingly, it is one object of the present invention to provide a hydraulic polycarboxylate cement composition of good compression strength.

Another object of the invention is to provide a cement composition in the form of powder having operational superiority in kneading when combined with water at the time of use.

A further object of the present invention is to provide a dental cement composition having a low tendency to deteriorate after having been applied in the oral cavity.

Briefly, these and other objects of the invention as hereinafter will become more readily apparent can be attained by providing a dental composition comprising a dental cement powder having silicon oxide as its essential constituent and a setting agent powder having polyacrylic acid as its essential constituent. The composition of this invention is provided in the form of a powder mixture, which has only to be kneaded with water (for example, tap water) to be ready for use. Only a small amount of water is necessary for kneading. The workability of the cement during kneading is also good on account of its low viscosity, and its compression strength is about equal to that of zinc phosphate cement because it contains silicon oxide in the dental cement powder portion.

BRIEF DESCRIPTION OF THE DRAWINGS

A more complete appreciation of the invention and many of the attendant advantages thereof will be readily attained as the same becomes better understood by reference to the following detailed description when considered in connection with the accompanying drawings, wherein.

DETAILED DESCRIPTION OF THE PREFERRED EMBODIMENTS

Figure 1:
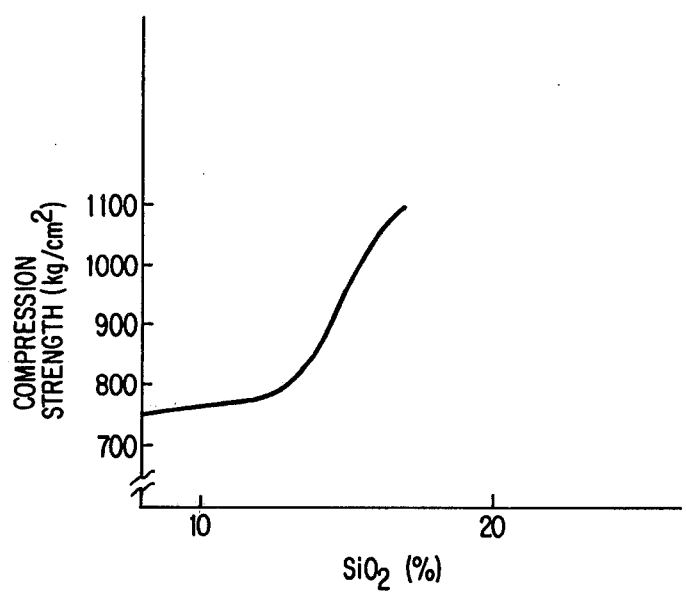
FIG. 1 is a plot of compression strength vs. silicon dioxide content.

The ingredients of the hydraulic cement composition of the invention will now be described in detail.

The cement powder containing silicon oxide may also include many other conventional ingredients. The percentage of silicon oxide contained in the powder may vary widely. However, it is normally desired that the powder contain not less than about 15% and up to about 80% of silicon oxide, most preferably 20 to 70%.

Another ingredient in the cement powder is zinc oxide. Generally speaking, a cement made from a powder containing silicon oxide has a tendency to deteriorate, once it has been kneaded with water and allowed to dry. In this respect, it resembles silicate cement. The same tendency may be seen in compositions analogous to the composition of the invention, and silicate-based compositions have in the past been known to deteriorate in the oral cavity. But when compounded with zinc oxide, this problem can be reduced to a level equal to that found for polycarboxylate cement, usually 0.3% deterioration.

Other ingredients may include a reactivity improver useful at the time of hydrate-kneading with the setting agent, as explained hereinafter. Suitable such compounds include aluminum oxide, inorganic fluorides (e.g., aluminum fluoride, cryolite, calcium fluoride), aluminum phosphate and the like. Magnesium oxide may also be added which has the function of improving the crushability of the sintered product obtained in preparing the dental cement powder.

The following table shows the preferred compounding proportions of each of the above-described ingredients.

|  | Compounding Proportions (% by weight) | Preferred Compounding Proportions (% by weight) |
| --- | --- | --- |
| Silicon oxide | 15–80 | 18–70 |
| Zinc oxide | 0–85 | 5–82 |
| Aluminum oxide | 0–25 | 5–20 |
| Inorganic fluoride | 0–60 | 5–50 |
| Aluminium phosphate | 0–20 | 5–15 |
| Magnesium oxide | 0–20 | 5–15 |

The reasons for selecting the above proportions for these ingredients will now be discussed.

Silicon oxide, although an indispensable ingredient in this invention, is not able to achieve the objects of the invention if it is present in an amount of less than 15 wt.%, because the composition then lacks sufficient physical strength, in particular compression strength, as shown in the example described hereinafter. Particularly when used for fillings, its preferred proportions should be not less than 15 wt.%. The physical strength of the dental cement is gradually improved in proportion to an increase in its content of silicon oxide, but when more than 80 wt.% is used, its reactivity with the setting agent, as described hereinafter, will be lowered, resulting in a decline in the physical strength of the cement. For this reason, it is recommended that the compounding proportion of silicon oxide be established in the range of 15 wt.% to 80 wt.%, preferably, it has been proved, 18 wt.% to 70 wt.%.

Zinc oxide need not always be compounded, but its inclusion is recommended on the ground that it is an effective ingredient for reducing deterioration (water-solubility) of the cement composition to a greater degree. It is desirable to have a high compounding proportion of zinc oxide especially for use in forming crowns or inlays. The additivity effect of zinc oxide is advantageous only up to 85 wt.%, above which it must lower the compounding proportion of silicon oxide below the minimum necessary to prevent the compression strength of the dental cement from deteriorating. For this reason, its especially preferred compounding proportion ranges from 5 wt.% to 82 wt.%.

Although inorganic fluoride, aluminum oxide, aluminum phosphate and the like have the function of improving the reactivity, as mentioned above, all of them are capable of contributing to deterioration when compounded in excess of the ranges mentioned above, so that they should be confined within the above-indicated limits. Among them, inorganic fluoride in particular has been proved to lower the compression strength when compounded at more than 60 wt.%.

As to magnesium oxide, while it enhances crushability even when compounded at above 20 wt.%, it also enhances deterioration at that level. Thus, it is preferably included in from 5 wt.% to 15 wt.%.

The cement powder of this invention is not subject to any restriction with respect to the mixing process or method of making. However, it is desirable to subject it to a heat treatment in order to maintain adequate strength for a dental cement. There is no limitation to the conditions for the heat treatment, but it is desirable that it be sintered at a temperature of from 1000° C. to 1250° C. for more than one hour, preferably, for about two hours. Since the sintered product is obtained in the form of a large conjoined mass, it must be crushed, preferably so as to obtain a powder with a particle diameter of 350 mesh or finer. The jet spraying method is usually recommended for this purpose.

The setting agent powder containing polyacrylic acid according to the present invention will now be described in further detail.

For the purposes of this invention, the term polyacrylic acid denotes either a homopolymer of acrylic acid, or a copolymer of acrylic acid and one or more compounds selected from the group consisting of $C_1$ to $C_6$ alkyl acrylates, $C_1$ to $C_6$ alkyl methacrylates and unsaturated carboxylic acids. The polymerization degree preferably ranges from 40 to 300. Preferred representatives of lower alkyl acrylates and lower alkyl methacrylates include methyl acrylate, ethyl acrylate, propyl acrylate, isopropyl acrylate, butyl acrylate, pentyl acrylate, tertiary butyl acrylate, hexyl acrylate, and the corresponding methacrylates. Preferred representatives of unsaturated carboxylic acids include maleic acid, itaconic acid, methacrylic acid, aconitic acid, fumaric acid, citraconic acid, mesaconic acid, and the like. The illustration here of examples, however, should not be construed as a definition of the limits of the present invention.

The moisture percentage of these setting agent powders is generally recommended to be less than 10%, since more than 10% moisture makes the material hard to pulverize, thereby vitiating the effectiveness of the invention. In addition, it is possible for a setting agent having an extremely high water content to incur the setting reaction when mixed in advance with the powder containing silicon oxide and left in storage. Therefore, when the water content of the setting agent powder is high, the agent should be stored separately from the powder containing silicon oxide, and mixed with it only at the time of actual use. In general, the lower the water content, the better the setting agent. However, since excessive dehydration would be uneconomical, the water content of the setting agent powder is normally not reduced below 0.05 wt.%.

It can be easily understood from the above discussion that it is desirable for the water content of the powder containing the silicon oxide to be regulated to a sufficient extent, as discussed above.

It is generally advisable for more silicon oxide powder to be used as compared with the quantity of setting agent powder used. The ratio of 95-50:5-50 is a preferred range. These powders may be uniformly mixed by the use of a ball mill, for example.

In actual use, the dental cement composition thus obtained is weighed to the required quantity and then, tap water is added at the ratio of powder to water of 2:0.45–0.60 (by weight), and the mixture is kneaded. In particular, the ratio of the powder to water is best at 2:0.45–0.52 for filling use, and at 2:0.53–0.60 for inlaying and crowning use, respectively.

The composition of this invention was preserved in a closed vessel for purposes of stability investigation. After a lapse of two years' preservation, it was proven that it did not deteriorate at all in quality, and maintained its very good properties. And even when a separate quantity of material was exposed to the air five times a day for five minutes every hour in the daytime, deterioration was not observed and the product remained stable even after the passage of one and one-half years.

Having generally described the invention, a more complete understanding can be obtained by reference to certain specific examples, which are included for purposes of illustration only and are not intended to be limiting unless otherwise specified.

In the Examples, the term "parts" used in the example means parts by weight.

EXAMPLE

A cement composition of this invention could be obtained by uniformly mixing a setting agent powder and a cement powder which were prepared separately according to the compounding ratio indicated in Table 1. For the cement powder used was one which was admixed, burned and then ground into 350-mesh-pass fine grain. This cement powder and the setting agent powder were treated in a ball mill for three hours together for uniform mixing. Each cement composition (mixed powder) thus obtained was kneaded in Standard preparation method together with a prescribed quantity of water. On measuring the setting time, compression strength, kneaded state and decay degree in imitation of JIS T-6602: "Dental zinc phosphate cement", each cement composition listed in Table 2 was confirmed to have superior characteristics in the capacity of a hydraulic dental cement.

Table 1

| Example No. | | | 1 | 2 | 3 | 4 | 5 | 6 | 7 |
|---|---|---|---|---|---|---|---|---|---|
| setting agent powder | composition (%) (parts by weight) | acrylic acid | 100 | 80 | 50 | 100 | 50 | 85 | 70 |
| | | itaconic acid | — | 20 | — | — | — | — | 20 |
| | | maleic acid | — | — | 40 | — | 50 | — | — |
| | | fumaric acid | — | — | 10 | — | — | — | 10 |
| | | aconitic acid | — | — | — | — | — | 15 | — |
| | polymer viscosity (cps) (50% aq. soln., at 25° C.) | | 15000 | 5000 | 10000 | 50000 | 5000 | 10000 | 3000 |
| | water content (%) | | 7 | 7 | 7 | 7 | 7 | 7 | 7 |
| cement powder | composition (%) (parts by weight) | $SiO_2$ | 120 (22.6) | 130 (25.3) | 95 (19.2) | 120 (24.0) | 120 (24.0) | 160 (32.0) | 233 (34.9) |
| | | ZnO | 70 (13.2) | 50 (9.8) | 95 (19.2) | 220 (44.0) | 220 (44.0) | 100 (20.0) | 207 (31.0) |
| | | $Al_2O_3$ | 100 (18.9) | 100 (19.5) | 100 (20.2) | 100 (20.0) | 100 (20.0) | 100 (20.0) | 100 (15.0) |
| | | $AlPO_4$ | 60 (11.3) | — | 73 (14.8) | — | — | — | 33 (5.0) |
| | | $CaF_2$ | 150 (28.3) | 83 (16.2) | 56 (11.3) | 60 (12.0) | — | 80 (16.0) | 47 (7.0) |
| | | $AlF_3$ | — | 33 (6.4) | — | — | — | — | — |
| | | Cryolite | 30 (5.7) | 117 (22.8) | 76 (15.4) | — | — | 60 (12.0) | 47 (7.0) |
| | | MgO | — | — | — | — | 60 (12.0) | — | — |
| | sintering temperature (°C.) | | 1150 | 1100 | 1150 | 1150 | 1250 | 1200 | 1150 |
| | sintering time (hrs.) | | 2 | 2 | 2 | 2 | 1.5 | 2 | 2 |
| setting agent powder/cement powder | | | 25/75 | 18/82 | 20/80 | 25/75 | 25/75 | 17/83 | 25/75 |

Table 2

| | powder/water | setting time (min.) | compression strength ($kg/cm^2$) | kneaded state | decay (%) |
|---|---|---|---|---|---|
| Example 1 | 2/0.48 | 5–6 | 1420 | good | 0.07 |
| " 2 | 2/0.55 | 5–6 | 1580 | " | 0.07 |
| " 3 | 2/0.52 | 5–6 | 1410 | " | 0.08 |
| " 4 | 2/0.55 | 5–6 | 1250 | " | 0.03 |
| " 5 | 2/0.55 | 5–6 | 1360 | " | 0.03 |
| " 6 | 2/0.48 | 5–6 | 1400 | " | 0.05 |
| " 7 | 2/0.55 | 5–6 | 1350 | " | 0.04 |

Comparative Example

In this Example 4 where cement powders were prepared only of silicon oxide and zinc oxide, and the relation of the compounding amount of silicon oxide to the compression strength was investigated. The results are shown in the following table.

TABLE 3

| $SiO_2$ (%) | Zno (%) | Compression Strength ($kg/cm^2$) |
|---|---|---|
| 0 | 100 | 750 |
| 13 | 87 | 800 |
| 16 | 84 | 1050 |

FIG. 1 represents the above table graphically, wherein the abruptly ascending tendency of the compression strength was confirmed when the compounding amount of silicon oxide was increased over 15%.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A hydraulic dental cement composition comprising a mixture of a dental cement powder containing from 18 to 70% by weight silicon oxide, from 9.8 to 82% by weight zinc oxide and at least one additional component selected from the group consisting of from 5 to 20% by weight aluminum oxide, from 5 to 50% by weight inorganic fluoride and from 5 to 15% by weight of aluminum phosphate; and a setting agent powder containing polyacrylic acid.

2. The composition of claim 1, wherein said dental cement powder containing silicon oxide is composed of the following ingredients:
   silicon oxide: 18–70% by weight
   zinc oxide: 9.8–82% by weight
   aluminum oxide: 5–20% by weight
   inorganic fluoride: 5–50% by weight
   aluminum phosphate: 5–15% by weight
   magnesium oxide: 5–15% by weight.

3. The composition of claim 1, wherein said dental cement powder is obtained by sintering a mixture of all said ingredients at a temperature of from 1000° to 1250° C. for at least one hour and by fine-crushing said mixture into grains of smaller than 350 mesh.

4. The composition of claim 1, wherein said dental cement powder is obtained by being fine-ground by being jet sprayed.

5. The composition of claim 1, wherein said setting agent powder contains a homopolymer of acrylic acid as its principal ingredient.

6. The composition of claim 1, wherein said setting agent powder contains a copolymer of acrylic acid with at least one member selected from the group consisting of lower ($C_1$–$C_6$) alkyl acrylate, lower ($C_1$–$C_6$) alkyl methacrylate, and unsaturated carboxylic acid.

7. The composition of claim 7, wherein said unsaturated carboxylic acid is at least one member selected from the group consisting of maleic acid, aconitic acid, fumaric acid, citraconic acid, mesaconic acid, itaconic acid, and methacrylic acid.

8. The composition of claim 1, wherein said setting agent powder comprises a polymer of 40 to 300 degrees of polymerization.

9. The composition of claim 1, wherein said setting agent powder contains less than 10% moisture.

10. The composition of claim 1, wherein the compounding ratio of said dental cement powder to said setting agent powder is 95-50:5-50.

11. A hydraulic dental cement composition comprising a mixture of a dental cement powder containing from 18 to 70% by weight silicon oxide, from 9.8 to 82% by weight zinc oxide and from 5 to 20% by weight aluminum oxide; and a setting agent powder containing polyacrylic acid.

12. The composition of claim 11, wherein said dental cement powder contains at least one additional component selected from the group consisting of from 5 to 50% by weight inorganic fluoride, from 5 to 15 by weight aluminum phosphate and from 5 to 15% by weight magnesium oxide.

* * * * *